United States Patent [19]
Akhavan-Tafti et al.

[11] Patent Number: 5,843,666
[45] Date of Patent: Dec. 1, 1998

[54] CHEMILUMINESCENT DETECTION METHODS USING DUAL ENZYER-LABELED BINDING PARTNERS

[75] Inventors: Hashem Akhavan-Tafti, Brighton; Katsuaki Sugioka; Yumiko Sugioka, both of Farmington Hills; Lekkala V. Reddy, Ann Arbor, all of Mich.

[73] Assignee: Lumigen, Inc., Southfield, Mich.

[21] Appl. No.: 749,595

[22] Filed: Nov. 15, 1996

Related U.S. Application Data

[63] Continuation-in-part of Ser. No. 300,367, Sep. 2, 1994.
[51] Int. Cl.$^6$ .................................................. G01N 33/535
[52] U.S. Cl. ................... 435/6; 435/7.1; 435/7.9; 435/7.91; 435/7.92; 435/18; 435/28
[58] Field of Search ................... 435/6, 7.1, 7.9, 435/7.91, 7.92, 18, 28

[56] References Cited

U.S. PATENT DOCUMENTS

| | | | |
|---|---|---|---|
| 4,563,417 | 1/1986 | Albarella et al. | 435/6 |
| 5,171,668 | 12/1992 | Sugiyama | 435/28 |
| 5,206,149 | 4/1993 | Oyama | 435/28 |
| 5,306,621 | 4/1994 | Kricka | 435/7.91 |
| 5,324,835 | 6/1994 | Yamaguchi | 544/234 |
| 5,491,072 | 2/1996 | Akhavan-Tafti | 435/28 |
| 5,516,641 | 5/1996 | Ullman | 435/6 |
| 5,523,212 | 6/1996 | Akhavan-Tafti | 435/28 |
| 5,552,298 | 9/1996 | Akhavan-Tafti | 435/28 |

FOREIGN PATENT DOCUMENTS 0185494  6/1986  European Pat. Off. .

OTHER PUBLICATIONS

Obzansky, D.M., et al., Clin. Chem., 37, 1513–8 (1991).
Wigle, D.A., et al., BioTechniques, 14, 562–3 (1993).
Tsuji, A., et al., Anal. Sci., 5, 497–506 (1989).
Johannsson, A., et al., Clin. Chim. Acta, 148, 119–24 (1985).
Cook, D.B., et al., Clin. Chem., 39, 965–71 (1993).
Serre, J.L., et al., Genomics, 11, 1149–51 (1991).
Martinelli, R.A., et al., Clin. Chem., 42, 14–18 (1996).
Thorpe, G., in Bioluminescence and Chemilumin escence, New Perspectives, 199–208 (1987).
Ii, M., et al., Biochem. Biophys. Res. Comm., 193(2), 540–5 (1993).
Laemmli, U.K., Nature, 227, 680–5 (1970).
Rabbitts, T.H., Nature, 372, 143–9 (1994).

*Primary Examiner*—Lora M. Green
*Attorney, Agent, or Firm*—Richard S. Handley

[57] ABSTRACT

Methods of detecting analytes or target species using two enzyme-labeled specific binding partners where the two enzymes function in concert to produce a detectable chemiluminescent signal are disclosed. The methods use a specific binding partner labeled with a hydrolytic enzyme to produce a phenolic enhancer in close proximity to a peroxidase-labeled second specific binding partner. The method is useful to detect and quantitate with improved specificity various biological molecules including antigens and antibodies by the technique of immunoassay, proteins by Western blotting, DNA by Southern blotting, RNA by Northern blotting. The method may also be used to detect DNA mutations and juxtaposed gene segments in chromosomal translocations and particularly to unambiguously identify heterozygous genotypes in a single test.

29 Claims, 9 Drawing Sheets

1 = N/N
2 = N/Δ
3 = Δ/Δ

1  2  3

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligomer"

( x i ) SEQUENCE DESCRIPTION: SEQ ID NO:1:

GATGAGCTTT ACCGCAG                                                      1 7

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligomer"

( x i ) SEQUENCE DESCRIPTION: SEQ ID NO:2:

ACCTCTGACA CATGCAG 17

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:3:

ACTTCACTTC TAATGATGAT TATG 24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:4:

CTCTTCTAGT TGGCATGCTT TGAT 24

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligomer"

( x i ) SEQUENCE DESCRIPTION: SEQ ID NO:5:

TATTCATCAT AGGAAACACC A 21

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligomer"

( x i ) SEQUENCE DESCRIPTION: SEQ ID NO:6:

ATGATATTTT CTTTAATGGT GCCA 24

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

-continued ( x i ) SEQUENCE DESCRIPTION: SEQ ID NO:7:

ATATCATCTT TGGTGTTTCC T                                                                           21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:8:

GAAATATCA TTGGTGTTTC C                                                                            21

CHEMILUMINESCENT DETECTION METHODS USING DUAL ENZYER-LABELED BINDING PARTNERS

REFERENCE TO RELATED APPLICATION

This application is a Continuation-In-Part of application Ser. No. 08/300,367 filed on Sep. 2, 1994.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. 2R44 DK47727-02 Awarded by the National Institutes of Health.

BACKGROUND OF THE INVENTION

(1) Field of The Invention

This invention relates to methods of detecting analytes or target species using two enzyme-labeled specific binding partners where the two enzymes function in concert to produce a detectable chemiluminescent signal. The invention further relates to a method for detecting analytes or target species using a peroxidase-labeled specific binding partner and a second specific binding partner labeled with a hydrolytic enzyme. Further, the invention relates to the use of the method to detect and quantitate with improved specificity various biological molecules including antigens and antibodies by the technique of immunoassay, proteins by Western blotting, DNA by Southern blotting, RNA by Northern blotting. The method may also be used to detect DNA mutations and chromosomal translocations.

(2) Description of Related Art (a) Chemiluminescent Reagents for Dual Enzyme Commonly assigned U.S. application Ser. No. 08/300, 367, the disclosure of which is fully incorporated herein by reference, discloses compositions comprising an acridancarboxylate derivative, a peroxide compound, and a protected enhancer compound which produce chemiluminescence by the action of a hydrolytic enzyme and a peroxidase enzyme. The hydrolytic enzyme removes a protecting group from the protected enhancer to produce a phenol compound which promotes the chemiluminescent peroxidase-catalyzed oxidation of the acridancarboxylate derivative.

U.S. Pat. No. 5,306,521, the disclosure of which is fully incorporated herein by reference, discloses compositions comprising a dihydrophthalazinedione, a peroxide compound, and a pro-enhancer compound which produce chemiluminescence by the action of a hydrolytic enzyme and a peroxidase enzyme. The hydrolytic enzyme removes a protecting group from the pro-enhancer to produce an enhancer compound which promotes the chemiluminescent peroxidase-catalyzed oxidation of the dihydrophthalazinedione.

Neither reference discloses the use of both enzymes as labels for use in assays. It is implicit in both publications that the hydrolytic enzyme be used in a limiting amount and the peroxidase be present in vast excess in order for the chemiluminescent oxidation to proceed with the highest intensity.

(b) Enzymatic Amplification Schemes

The aforementioned U.S. Pat. No. 5,306,621 to Kricka describes a method for the enzymatic generation of an enhancer from an inactive pro-enhancer for the HRP-catalyzed chemiluminescent oxidation of luminol. No disclosure or suggestion is made of the use of acridans as chemiluminescent substrates. The relatively poor sensitivity of this method ($10^{-16}$ mol of alkaline phosphatase, (AP)) reported is insufficient for many applications.

A coupled enzyme cascade reaction for the colorimetric detection of AP has been reported (D. M. Obzansky et al, Clin. Chem., 37, 1513–8 (1991)). In this scheme, AP generates a substance which reacts with an inactive form of a second enzyme, converting it to its active state. The second enzyme reacts with its own substrate producing $H_2O_2$. The $H_2O_2$ is detected through a subsequent colorimetric procedure. No disclosure or suggestion of chemiluminescent detection is made.

A chemiluminescent Western blot method has been reported wherein bound HRP-antibody conjugate catalyzes a reaction leading to the deposition of a biotin-phenol conjugate on the surface of the membrane. The bound biotin is used to capture additional HRP-streptavidin conjugate. The captured enzyme was detected by luminol chemiluminescence (D. A. Wigle, N. N. Radakovic, S. L. Venance, S. C. Pang, BioTechniques, 14, 562–3 (1993)). No disclosure or suggestion is made of the use of acridans as chemiluminescent substrates.

Several bioluminescent and chemiluminescent reactions involving multiple enzymes are known (A. Tsuji, M. Maeda, H. Arakawa, Anal. Sci., 5, 497–506 (1989)). In most of these procedures, careful consideration of the mode of action reveals that, in contrast to the present invention, only one amplification step occurs. All subsequent steps merely form an electron-relay system for effecting the ultimate luminescent reaction. Only the colorimetric method based on the generation of $NADP^+$ by AP is truly a dual amplification process (A. Johannsson, C. J. Stanley, C. H. Self, Clin. Chim. Acta, 148, 119–24 (1985)). A fluorimetric assay based on the same principle is also known (D. B. Cook, C. H. Self, Clin. Chem., 39, 965–71 (1993)). Neither reference teaches or suggests the use of chemiluminescence.

(c) Detection of Cystic Fibrosis Mutations

Several different methods of molecular detection of Cystic Fibrosis (CF) mutations have been reported. These include allele-specific oligonucleotide hybridization, allele specific polymerase chain reaction (PCR) amplification system, amplification refractory mutation system, polyacrylamide gel electrophoresis of PCR products of exon 10 (for $\Delta F_{508}$), PCR amplification followed by restriction enzyme digestion, multiplex PCR amplification, single strand conformation polymorphism and reverse dot blot hybridization (Serre J. L., Taillandier A., Mornt E., Simon-Buoy B., Boue J., Boue A., Genomics, 11, 1149–51 (1991)). An ELISA-type detection format where one oligonucleotide was immobilized on paramagnetic particles and another was labeled with an acridinium ester has recently been reported (Martinelli R. A., Arruda J. C., Dwivedi P., Clin. Chem., 42, 14–18 (1996)). These methods have evolved over a period of time as simultaneous detection of multiple mutations was warranted with the discovery of many more CF mutations. None of these methods utilize two enzyme-labeled reporter probes.

Chemiluminescent detection systems are rapidly gaining popularity as safer alternatives to isotopic methods in molecular diagnostics with equal sensitivity and specificity. In addition, they offer versatility of detection because of the availability of different haptens for labeling the probes, the anti-hapten antibodies conjugated with either AP or horseradish peroxidase (HRP), and their respective chemiluminescent substrates.

In spite of these advances, a single test which provides an unequivocal positive identification of $N/\Delta F_{508}$ genotype would be desirable. This may be valuable for distinguishing normal from carriers in population screening and heterozygous from homozygous for CF $\Delta F_{508}$ in prenatal and neonatal diagnosis.

(d) Dual DNA Probe Assays

U.S. Pat. No. 5,516,641 discloses DNA probe capture assays employing two probes complementary to different non-contiguous sequence regions of a nucleic acid analyte. In the methods disclosed, one probe is capable of immobilization and is not detectably labeled and the other probe capable of having a detectable label. The two probes are hybridized and then subsequently covalently joined by chemical, photochemical or enzymatic means.

European Patent Application No. EP 0 185 494 A2 discloses DNA probe assays employing two probes complementary to different contiguous sequence regions of a nucleic acid analyte. Neither publication discloses or suggests the use of two different enzyme labels on the two probes acting in concert to produce a chemiluminescent signal.

IN THE DRAWINGS

Figure 4A:
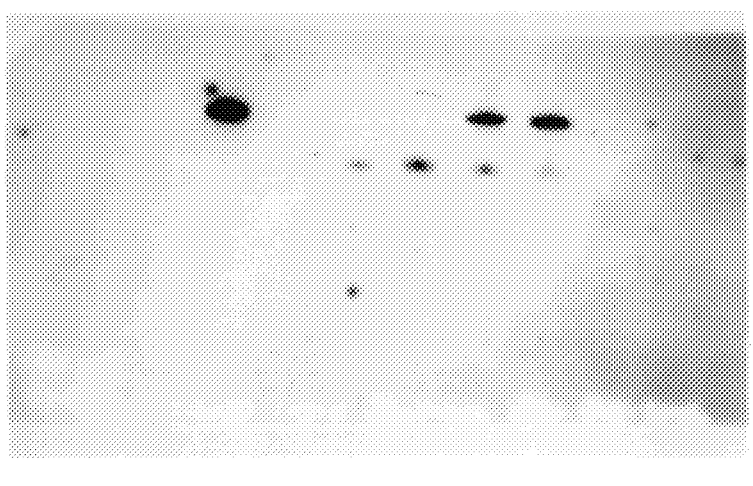
Figure 4B:
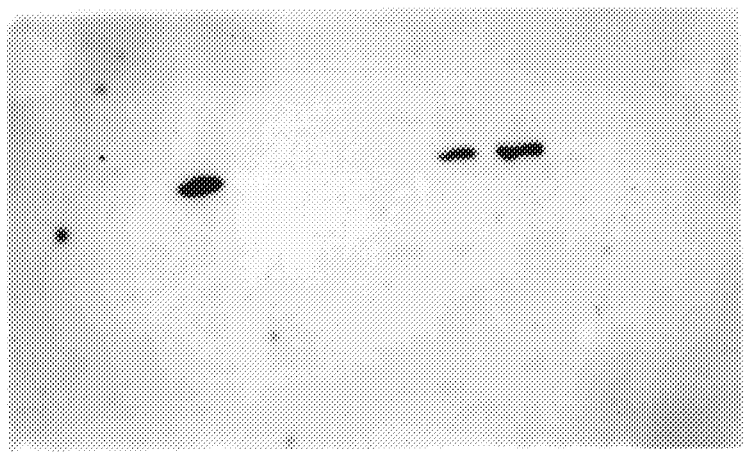

FIGS. 4A and 4B are digital images of x-ray films from an experiment detecting the $\Delta F_{508}$ mutation in samples which are homozygous or heterozygous for the mutation and not in a sample which is homozygous normal by the ligation of 21mer and 24mer probes. In 4A, the electrophoresis gel was run a short distance which did not separate the 21mer and 24mer oligonucleotides. In 4B, the electrophoresis gel was run a longer distance which separated the 21mer and 24mer oligonucleotides.

Figure 5:
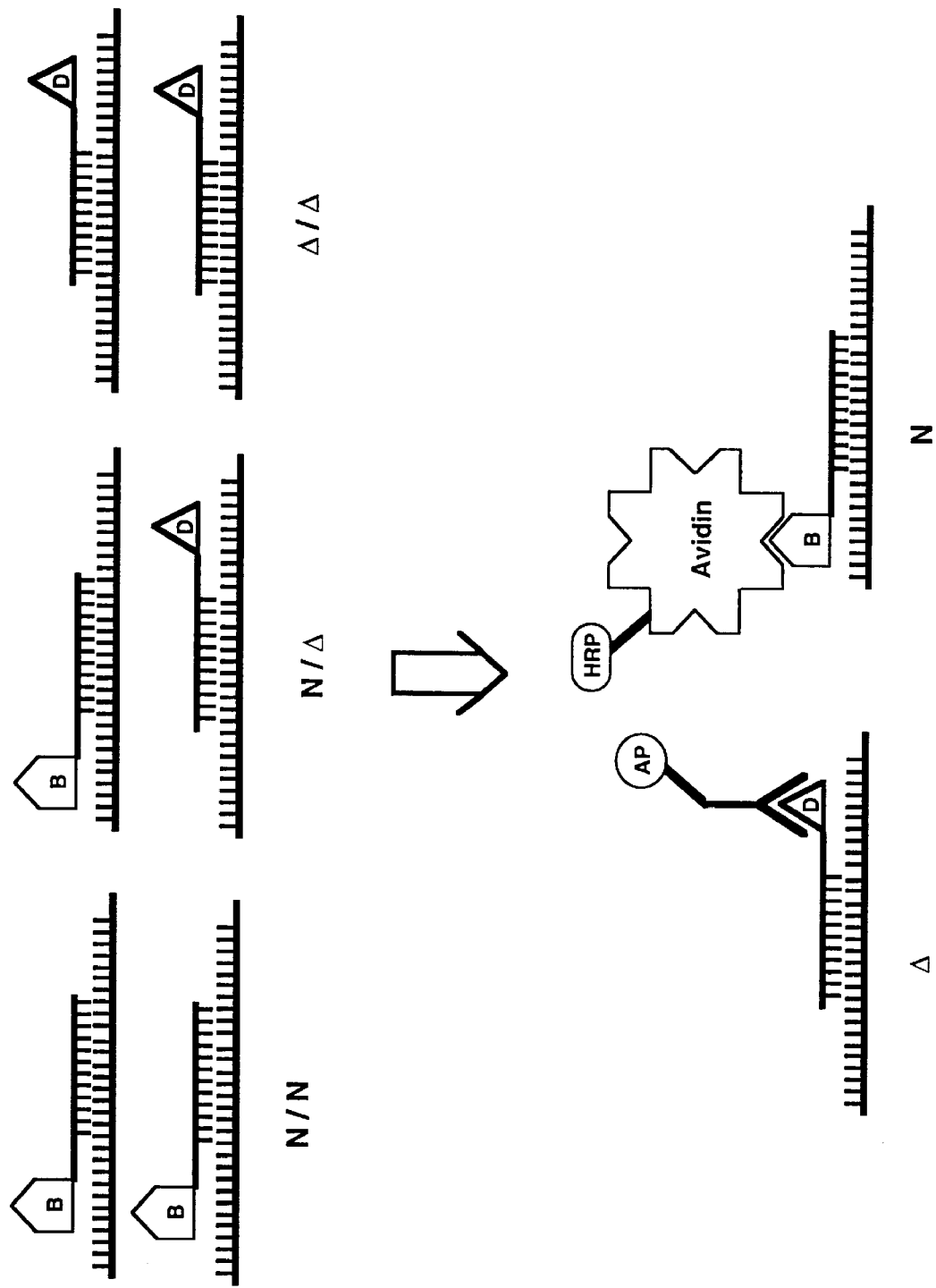

FIG. 5 is a schematic drawing of a DNA hybridization assay according to the present invention to detect the $\Delta F_{508}$ mutation only in a sample which is heterozygous for the mutation and not in samples which are homozygous normal or homozygous for the mutation.

Figure 6:
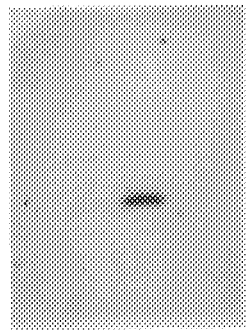

FIG. 6 is a digital image of an x-ray film from an experiment detecting the $\Delta F_{508}$ mutation only in a sample which is heterozygous for the mutation and not in samples which are homozygous normal or homozygous for the mutation.

Figure 7:
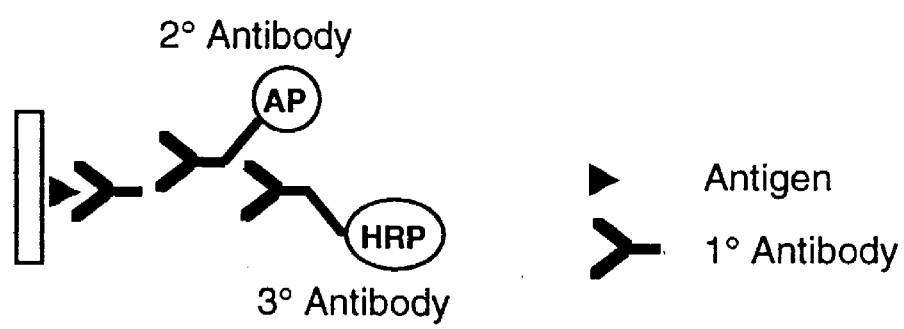

FIG. 7 is a schematic drawing of the immunological reaction used in a Western blot employing dual enzyme-labeled antibodies according to the present invention.

Figure 8:
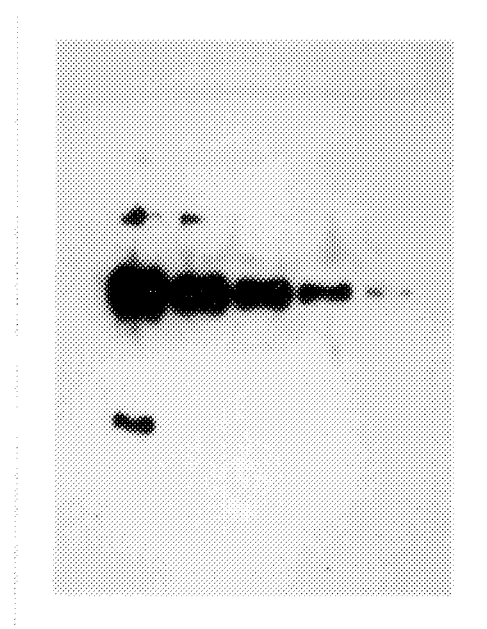

FIG. 8 is a digital image of an x-ray film from a Western blot of human HIV γ-gp120 with an AP-labeled 2° antibody and an HRP-labeled 3° antibody chemiluminescent detection conducted according to the present invention.

OBJECTS

It is therefore an object of the present invention to provide a method for simultaneously detecting the presence of two target species in a sample using two enzyme-labeled probes acting in concert to generate chemiluminescence. It is another object of the present invention to provide a chemiluminescent method for the detection of genetic mutations. It is another object of the present invention to provide a chemiluminescent method for the detection of chromosomal translocations. It is another object of the present invention to provide a chemiluminescent method for the differentiation of heterozygotes from homozygotes for a genetic condition. It is another object of the present invention to provide a chemiluminescent method for the detection by a sandwich immunoassay of protein antigens presenting at least two epitopes. It is another object of the present invention to provide a chemiluminescent Western blotting method using two enzyme-labeled antibodies. It is still another object of the present invention to provide a method to simultaneously detect the presence of an infectious agent in a clinical specimen along with the expression of host factors such as cytokines in response to the presence of the infectious agent. The detection medium in the above methods may take the form of e.g. an immunoassay on a test strip or on the surface of a bead, well or test tube, the detection of a band of protein on a Western blotted membrane the detection of a band of DNA on a Southern blotted membrane or in a DNA hybridization assay on a filter.

DESCRIPTION OF THE PREFERRED EMBODIMENTS

Definitions

Binding pair—two molecules or portions thereof which have a specific binding affinity for one another by virtue of multiple noncovalent attractions. Specific binding pairs are well known in the art and include by way of illustration antigen-antibody, hapten-antibody, antibody-antibody, complementary strands of DNA, DNA-RNA duplexes, DNA-complementary oligonucleotide, RNA-complementary oligonucleotide, DNA-anti-DNA antibody, DNA-DNA binding protein, biotin-avidin or streptavidin, receptor-ligand, protein A-IgG and lectin-carbohydrate.

Chemiluminescent peroxidase substrate—compounds which undergo an oxidation reaction in the presence of a peroxidase and a peroxide which results in the production of visible light. Several chemiluminescent peroxidase substrates are known in the art as described in (Kricka Ref). The most commonly used include the amino-substituted dihydrophthalazinediones such as luminol, isoluminol, N-alkyl and N,N-dialkylamino derivatives of luminol and isoluminol, 5-amino-6,7,8-trimethoxydihydrophthalazinedione and the benzo-fused homologs such as 7-dimethylaminonaphthalazinedione. Other chemiluminescent peroxidase substrates include the pyridazinoquinoxalinones as disclosed in U.S. Pat. No. 5,324,835. Still other chemiluminescent peroxidase substrates include the hydroxy-substituted dihydrophthalazinediones such as 5-hydroxy- and 6-hydroxyphthalazinediones and the hydroxynaphthalazinedione as disclosed in U.S. Pat. No. 5,552,298 assigned to the assignee of the present application, and a class of N-alkylacridan-9-carboxylate derivatives including esters, thioesters and sulfonimides as disclosed in commonly assigned U.S. Pat. Nos. 5,491,072 and 5,523,212 and U.S. application Ser. No. 08/205,093 now U.S. Pat. No. 5,593,845

Closely spaced relationship—as used in describing the proximity of co-immobilized enzyme labels used in the methods of the present invention, constrained to lie in a region near enough to the other enzyme label so that the enzymatic reaction product of the hydrolytic enzyme is available to enhance the reactivity of the peroxidase enzyme. This can be accomplished by physically binding the two enzyme labels to the same molecular species by direct or indirect means. The closely spaced relationship can also result when a physical mixture of two distinct target molecules each bound to an enzyme-labeled specific binding partner are physically immobilized in the same region of a solid support.

Enhancer—a substance which promotes or prolongs the oxidative or peroxidative function of a peroxidase enzyme. The most effective enhancers are certain aromatic amines and phenols. Phenolic compounds known to enhance peroxidase reactions are described in G. Thorpe, L. Kricka, in *Bioluminescence and Chemiluminescence, New Perspectives*, J. Scholmerich, et al, Eds., pp. 199–208 (1987), M. Ii, H. Yoshida, Y. Aramaki, H. Masuya, T. Hada, M. Terada, M. Hatanaka, Y. Ichimori, *Biochem. Biophys. Res. Comm.*, 193(2), 540–5 (1993), and in U.S. Pat. Nos. 5,171,668 and 5,206,149 which are incorporated herein by reference. Preferred enhancers are selected from the group consisting of substituted phenols, unsubstituted and substituted naphthols, including but not limited to: p-phenylphenol, p-iodophenol, p-bromophenol, p-chlorophenol, 2,4-dichloro-phenol, p-imidazolylphenol, p-thiazolylphenol, p-hydroxy-acetanilide, p-hydroxycinnamic acid, (p-cyanomethylthio)-phenol and ring halogenated derivatives thereof, phenolindophenol, 2-naphthol, 6-bromo-2-naphthol 6-hydroxybenzothiazole, 2-cyano-6-hydroxybenzothiazole, firefly luciferin and dehydroluciferin.

Enzyme label—a functional enzyme associated with a member of a specific binding pair. The enzyme may be covalently linked to the specific binding partner, e.g. an enzyme-antibody conjugate or an enzyme-oligonucleotide conjugate. The enzyme may be indirectly linked or associated with the specific binding partner of the target by the use of an auxiliary specific binding partner to which the enzyme is covalently linked. An example of the latter relationship would be the use of a biotin-labeled oligonucleotide probe for a certain DNA sequence associated with an enzyme-avidin conjugate.

Genetic disease—pathologic condition caused by a genetic defect such as a mutation or a series of mutations. The mutation may be a point mutation, a single base substitution, a deletion, an insertion, a duplication or a transposition of bases or a combination of the above. Depending on the site or position and type of mutation, the mutant gene may or may not be expressed, if expressed, it may lead to the production of truncated or non-functional protein products or proteins with an altered amino acid sequence. Certain genetic mutations are recessive whereby both mutant alleles or copies of the gene on the homologous chromosomes must be present for disease symptoms to occur. other genetic diseases are dominant whereby only one copy of the gene needs to bear the mutation for disease symptoms to occur. Individuals with one copy of the recessive mutant gene are carriers without any disease but can still transmit a copy of the mutant gene to offspring.

Hydrolytic enzyme—are enzymes which catalyze the hydrolytic cleavage of various groups. Representative members include;

esterases such as carboxyl esterase, acetylcholinesterase, butyrylcholinesterase and cholinesterase, glycosidases, such as galactosidase, glucosidase, glucuronidase, lactase, and N-acetylglucosaminidase, lipase, phospholipase, plant or animal phosphatases, including acid and alkaline phosphatases, protease enzymes such as chymotrypsin, trypsin, papain and pepsin and sulfatase enzymes.

Peroxidase enzyme—enzymes belonging to class EC 1.11.1.7 including horseradish peroxidase, cytochrome C peroxidase, glutathione peroxidase, microperoxidase, myeloperoxidase, lactoperoxidase, *Arthromyces ramosus* peroxidase (ARP) and soybean peroxidase.

Peroxide—compounds which act as a source of hydrogen peroxide which function as the primary substrate of the peroxidase. Exemplary peroxides include hydrogen peroxide, urea peroxide and perborate salts, especially sodium perborate.

Sample—materials upon which the methods of the present invention are performed to detect an analyte and includes human and animal bodily fluids, such as blood, serum, urine, saliva, sputum, CSF, seminal fluid and cell lysate, as well as food samples, water samples, plant samples, microbiological specimens and forensic specimens. Other types of samples as would occur to one of ordinary skill in the art are considered to be within the scope of the invention.

Solid support—test medium on which assay methods of the present invention can be carried out. Such supports include test strips, blotting membranes, filters, microwells, test tubes, beads and the like as are known in the art of assays. The supports must be capable of capturing or immobilizing the target species-specific binding agent pair by physical adsorption or covalent linkage or both.

Target species—molecule or portion thereof whose presence is being probed. Target species must be capable of binding with a substance with which there is a specific binding affinity. In one embodiment, the target species will be bound to two different specific binding partners, each of which has a specific binding affinity. Exemplary target species include, nucleic acids such as ssDNA, dsDNA, RNA, oligonucleotides, proteins, antibodies, antigens, haptens, cell surface receptors, ligands, hormones, viruses, bacteria and the like.

The present invention relates to a method for simultaneously detecting a first and second target species in a sample suspected of containing the two target species by a chemiluminescent reaction comprising:

(a) contacting the sample with a first specific binding partner for the first species and a second specific binding partner for the second species to thereby form a first binding pair and a second binding pair;

(b) providing a hydrolytic enzyme as a label for the first binding pair and providing a peroxidase enzyme as a label for the second binding pair;

(c) providing for reaction with the first and second binding pair a chemiluminescent peroxidase substrate, a peroxide compound and a protected enhancer compound of the formula ArOX wherein X is a group which is removable by the hydrolytic enzyme to produce a phenolic enhancer compound ArOH which is functional as an enhancer of peroxidase activity; and (d) allowing the hydrolytic enzyme to react with the protected enhancer compound to produce the enhancer compound which enhances the activity of the peroxidase with the peroxide and the peroxidase substrate and thereby produce chemiluminescence, wherein the production of chemiluminescence indicates the presence of both target species in the sample.

In the methods of the present invention, the combined action of both a hydrolytic enzyme and a peroxidase enzyme which are maintained in a closely spaced relationship to each other operates to produce a detectable chemiluminescent signal for the purpose of detecting the presence, location or amount of an analyte or target species in a sample. It is believed that the enforced proximity of the two enzymes leads to improved assay sensitivity and specificity. Previous chemiluminescent two enzyme assays using a hydrolytic enzyme as a label and the peroxidase as a reagent in a solution required much higher concentrations of the peroxidase for optimum performance. In the present methods, the ratio of peroxidase/hydrolytic enzyme ranges from about 1:1 to about 1:5.

The method for simultaneously detecting the presence of two target species in a sample using two enzyme-labeled probes can be used advantageously in several types of tests. One area of application is in a chemiluminescent method for the detection of genetic mutations. In one embodiment, a DNA sample, which can be crude or purified genomic DNA, a restriction digest, DNA amplified by PCR, LCR or other known amplification methods, or RNA is subjected to the method of the present invention to detect the presence of a mutation selected from a point mutation, a single base substitution, a deletion, an insertion, a duplication, a transposition of bases or a combination of the above. Two probes complementary to the target region are hybridized, wherein at least one of the probes is complementary to a region containing either the normal or mutant sequence. The probes can be directly labeled with the two requisite enzymes or can be labeled with a member of a specific binding pair and subsequently bound with an enzyme conjugate of the complementary specific binding partner.

In another embodiment of the present methods for detecting deletional mutations, two differently labeled probes of m and n bases, respectively, are hybridized such that, after hybridization to the target mutant sequence, the 3'-end of the first probe lies immediately adjacent to the 5'-end of the second probe. The two probes are then ligated using a ligase to form a new probe of length m+n bases bearing both labels. The presence of a base or several bases in the normal target sequence between the hybridized first and second probes will result in a gap preventing the ligation of the hybridized oligonucleotides. The detection of the longer ligated probe indicates the presence of the mutant target sequence (m+n bases) in the sample.

Another area of application is in a method for the detection of juxtaposed genes in chromosomal translocations. Associated with some pathologic conditions, including certain malignancies is the occurrence of altered DNA sequences in which genes that are normally present on two different chromosomes recombine such that the two gene sequences are juxtaposed on the same chromosome. To test for this type of chromosomal abnormality, according to a method of the present invention, a probe for the first gene directly or indirectly labeled with a hydrolytic enzyme and a probe for the second gene directly or indirectly labeled with a peroxidase are hybridized to the DNA suspected of containing the translocation. Reaction with the chemiluminescent reagent produces a signal only when the two sequences are present in the same translocated portion of DNA.

More particularly the methods of the present invention can be used to provide a chemiluminescent method for the differentiation of heterozygotes from homozygotes for a genetic condition. Since two copies of a chromosome containing a DNA sequence of interest are present in a sample, the two enzyme label technology embodied in the present methods provides a means for distinguishing heterozygotes from either homozygote. In many genetic diseases with a recessive gene mutation, the two homozygous genotypes are readily disinguished from each other clinically asbeing normal or having a disease phenotypes. The heterozygous genotype found in phenotypically normal carriers is determined by genetic analysis or analysis of familial inheritance patterns. Application of a test using a peroxidase-labeled probe for the normal genotype and a hydrolytic enzyme-labeled probe for the mutation genotype (or vice versa) leads to unambiguous identification of the heterozygous genotype. Reaction with the chemiluminescent reagent produces a signal only when the normal and mutant sequences are both present in the DNA sample.

It is another object of the present invention to provide a chemiluminescent method for the detection by a sandwich immunoassay of protein antigens presenting at least two epitopes. Sandwich immunoassays are well known in the art. Heterogeneous sandwich immunoassays involve the use of a first antibody (capture antibody) immobilized on a solid phase which binds to a first epitope on the analyte. A second antibody binds to a second epitope of the analyte to form the so-called sandwich. To adapt the chemiluminescent detection methods of the present invention to this type of assay, requires only that one antibody be labeled with a peroxidase enzyme and the other with a hydrolytic enzyme. Reaction of the immune complex with the chemiluminescent reagent produces a signal emanating from the solid phase.

It is another object of the present invention to provide a chemiluminescent Western blotting method using two enzyme-labeled antibodies. Various formats for the immunological binding of two antibodies with different enzyme labels are possible. The first of these formats is shown in FIG. 7. The two requisite enzyme-labeled antibodies are supplied as a 2° antibody /3° antibody stack as shown. An alternate format would be to use a mixture of hydrolytic enzyme-labeled and peroxidase-labeled 2° antibodies which compete for binding to the 1° antibody. A third format would use a 1° antibody with one enzyme label and a 2° antibody with the other enzyme label. In each format, the two different enzymes are localized at the site where the antigen is fixed, so that the chemiluminescent reaction can proceed.

It will be understood by the skilled artisan on the basis of the preceding description that the detection medium in the above methods may take the form of a test strip, the surface of a bead, well or test tube, the detection of a band of protein on a Western blotted membrane the detection of a band of DNA on a Southern blotted membrane or in a DNA hybridization assay on a filter.

Detecting a target species can take the form of a quantitative assay for determining the amount of the target species in the sample. The detection can also be qualitative in nature in which case a simple yes/no type of answer can be obtained. The methods of the present invention can also be employed in a test to determine the location of an analyte or target species since the enzyme labels are localized or immobilized in a region of space.

Preferred enhancers to be generated by the action of the hydrolytic enzyme on the protected enhancer include phenolic compounds. Phenolic compounds known to enhance peroxidase reactions are well known in the art and are listed, in part, in co-pending U.S. application Ser. No. 08/300,367. Other preferred enhancers known in the art in addition to those mentioned in the co-pending application include, without limitation, p-imidazolylphenol, p-thiazolylphenol, p-hydroxyacetanilide, (p-cyanomethylthio)-phenol and its ring halogenated derivatives, phenolindo-phenol and 4-hydroxy-3-methoxybenzylidenecyclopentenedione.

The chemiluminescent substrate is typically supplied in an aqueous solution containing other components such as buffer salts, metal ions and preservatives which are necessary or useful for enzyme function and for storage and manufacturing considerations. In a preferred embodiment the chemiluminescent substrate is supplied in a reagent composition comprising a buffer, the peroxide and the protected enhancer. Buffer pH will be in the range of about 7 to 10 and more preferable about 8 to 9.5. The composition can further comprise metal ions beneficial for enzyme function and preservatives to prevent microbial growth. The composition can further comprise suppressing agents which reduce background chemiluminescence from the reagent composition. Exemplary background suppressing agents include nonionic surfactants, nonionic water-soluble polymers such as polyether polyols and proteins such as serum albumin and non-fat milk. The composition can be prepared in advance and stored for later use or be assembled as needed from two or more containers containing the components. For example it may be desirable to store the chemiluminescent substrate separately from the peroxide.

Several types of chemiluminescent peroxidase substrate compounds can undergo the necessary oxidation reaction in the presence of a peroxidase and a peroxide which results in the production of visible light. Preferred reagents include luminol 5-hydroxyphthalazinedione and N-alkylacridan-9-carboxylate derivatives including esters, thioesters and sulfonimides as disclosed in commonly assigned U.S. Pat. Nos. 5,491,072 and 5,523,212 and U.S. application Ser. No. 08/205,093 now U.S. Pat. No. 5,593,845 having the general formula:

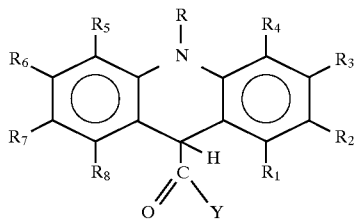

wherein R is selected from alkyl, heteroalkyl and aralkyl groups, wherein $R_1$ to $R_8$ are selected independently from groups which allow the production of light and wherein adjacent pairs of groups $R_1$ to $R_8$ may constitute the group CH=CH—CH=CH thereby forming a benzo-fused ring and wherein Y is a leaving group. Preferred acridancarboxylate derivatives have the formula:

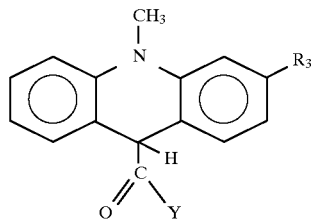

wherein Y is a di- or polyhaloaryloxy group and wherein $R_3$ is H or a methoxy group.

Hydrolytic enzymes useful in the practice of the present invention are those which can be linked or conjugated to a specific binding partner and function to convert a protected enhancer compound to the free enhancer. Preferred hydrolytic enzymes include alkaline phosphatase, β-galactosidase, β-glucosidase, β-glucuronidase and carboxyl esterase. Alkaline phosphatase is most preferred.

At least one hydrolytic enzyme must be supplied as the label on one of the two enzyme-labeled specific binding partners. However more than one of the same enzyme molecule may be supplied and it is frequently advantageous to do so. For example, when the specific binding partner to be labeled is a high molecular weight or polymeric species, such as an antibody or nucleic acid, it is desirable to have multiple enzyme labels to increase sensitivity. Moreover, some labeling techniques do not permit the selective attachment of just one label. The enzyme may be indirectly linked or associated with the specific binding partner of the target by the use of an auxiliary specific binding partner to which the enzyme is covalently linked. An example of the latter relationship would be the use of a biotin-labeled oligonucleotide probe for a certain DNA sequence bound with an enzyme-avidin conjugate.

When nucleic acid probes are employed in the practice of the present methods the probe length may be any suitable length which provides specific binding and is capable of bearing at least one label. Synthetic oligonucleotide probes can be from about 10–200 bases, more commonly 15–50 bases. Probes produced by cloning can be up to a few thousand bases in length. In general, shorter probes of 20–25 bases provide better specificity and longer probes of several hundred bases long increase the sensitivity because of the ability to attach more labels. Methods of probe production and labeling are generally known in the art and do not form a part of the inventive method per se.

Suitable target species for which the detection methods of the present invention can be applied include molecules or portion thereof which are capable of binding with another substance with which it has a specific binding affinity. Preferred target species include, nucleic acids such as ssDNA, dsDNA, RNA and oligonucleotides, proteins, antibodies, antigens, haptens, cell surface receptors, ligands, hormones, viruses, bacteria and the like. Genetic sequences can represent the target species.

For the identification of a chromosomal translocation, probes to two nucleic acid sequences which will reside on a common fragment as a result of the rearrangement are employed. Exemplary gene rearrangements resulting from chromosomal translocations and the associated disease syndrome are listed in Table 1. A more thorough compilation can be found in T. H. Rabbitts, Nature, 372, 143–9 (1994).

TABLE 1

Examples of Gene Rearrangements in Chromosomal Translocations

| Rearranged Genes | Translocation | Disease |
| --- | --- | --- |
| c-myc-IgH | t (8;14) (q24;q32) | Burkitt's Lymphoma |
| BCL-2-IgH | t (14;18) (q32;q21) | Follicular Lymphoma |
| PML-RARA | t (15;17) (q21;q11.22) | Acute Promyelocyctic Leukemia |
| FL11-EWS | t (11;22) (q24;q12) | Ewings Sarcoma |
| AF4-MLL | t (4;11) (q21;q23) | Acute Lymphocyctic Leukemia |

For the identification of a simpler mutation such as a deletion of a few bases or a single base substitution, the two target species will be the normal sequence region without the mutation and the region with the mutant sequence.

TABLE 2

Examples of Single Gene Disorders with Autosomal Recessive Mutations.

| Disease | Mutation Type |
| --- | --- |
| Cystic Fibrosis | 3 Base pair deletion ($\Delta F_{508}$) + ca. 500 others |
| α-Thalassemia | Single base mutation, deletion |
| β-Thalassemia | Single base mutation |
| Sickle Cell Anemia | Single base mutation (A→T) |
| Tay-Sachs | 4 Base pair deletion, single base mutation |

Other proteins and high molecular weight analytes which present at least two epitopes for immunological recognition include for example antigens, immunoglobulins, hormones, including thyrotropin (TSH), alpha-fetoprotein (AFP), carcinoembryonic antigen (CEA), ferritin, serum albumin, C-reactive protein and insulin. Methods of the present invention can be applied in a Western blot format or a sandwich immunoassay format using two enzyme-labeled antibodies for the detection or quantitation of such analytes in a sample. Exemplary techniques will be presented below.

The method may also be used to simultaneously detect the presence of an infectious agent in a clinical specimen along with the expression of host factors such as cytokines in response to the presence of the infectious agent. The method may also be used to simultaneously detect the presence of two different infectious agents in a clinical specimen by detecting their DNA, RNA, antigens or the antibodies produced in response to the infection.

Specific Embodiments

The present invention has as one objective to develop methods for specific and rapid detection of genetic mutations such as the CF $\Delta F_{508}$ mutation and their genotypes, particularly to identify heterozygous patients (carriers) in a single test. Using the methods of the present invention, we have developed two methodologies for differentiating the $\Delta F_{508}$ genotypes. One method depends on the specific detection of ligated product of two uniquely labeled oligonucleotide primers that are complementary to the flanking regions of the $\Delta F_{508}$ mutation. In this method, a pair of oligonucleotides designed to anneal to the flanking regions of $\Delta F_{508}$ mutation are differentially labeled with the haptens biotin or fluorescein and ligated using the template DNA of wildtype (N/N), heterozygous (N/$\Delta F_{508}$) and homozygous ($\Delta F_{508}/\Delta F_{508}$) genotypes. The ligated product containing both the labels is detected by first binding with anti-biotin-HRP (or avidin-HRP) and anti-fluorescein-AP followed by reacting with the dual substrate. As expected, the ligation products were detected only in N/$\Delta F_{508}$ and $\Delta F_{508}/\Delta F_{508}$ genotypes but not in N/N where the ligation is precluded by the presence of three intervening nucleotides.

In another format, the three genotypes are hybridized on a membrane simultaneously with uniquely labeled (biotin or digoxigenin) oligonucleotides designed to bind the normal and mutant alleles. Upon treating with HRP and AP-conjugated specific binding partners, followed by reacting with a composition comprising a chemiluinescent peroxidase substrate, a peroxide and a protected enhancer, only the band from N/$\Delta F_{508}$ genotype emitted a strong signal because of the binding of both oligonucleotides.

The utility of a novel dual probe/dual substrate method for differentiating the genotypes of $\Delta F_{508}$ mutation of cystic fibrosis is demonstrated in the examples presented hereinafter. The ligation and hybridization formats are exemplary. Other formats may be devised for the detection of mutations as well. An ELISA-type detection format can be used where the sample DNA is immobilized and a pair of enzyme-labeled oligonucleotide probes are hybridized and optionally ligated. Alternatively, one of the enzyme-labeled oligonucleotides can be immobilized as a capture probe. After or concurrently with capture of target DNA, the other enzyme-labeled oligonucleotide is hybridized.

The assay methods presented here can be utilized by such modifications as will be apparent to one of skill in the art for the detection of single base substitution mutations of CFTR and other genes. In order to more fully describe the various aspects of the present invention, the following non-limiting examples describing particular embodiments are presented for purposes of illustration of the invention. The scope of the invention is limited only by the appended claims.

EXAMPLES

Example 1

Detection of Two Co-immobilized DNA Sequences

We have developed a novel chemiluminescent detection system for DNA analytes with excellent specificity through the use of dual enzyme labels. The detection scheme is based on our discovery that an enzymatically liberated phenol enhancer markedly increases the intensity and duration of light emission from horseradish peroxidase (HRP) catalyzed oxidation of N-alkylacridan-9-carboxylic acid derivatives. Binding of a pair of differentially labeled oligonucleotide probes by a target on a solid phase places both enzymes in close proximity. An AP-labeled probe generates the phenol enhancer in situ from a phosphate derivative in the vicinity of a peroxidase-labeled probe. The phenol enhancer catalyzes the light producing reaction. Nonspecific signal only arises if both probes bind unspecifically at the same site.

In this format, a mixture of two labeled DNA samples bearing different marker enzymes were first co-immobilized on nylon membrane. HindIII DNA fragments end-labeled with fluorescein or photochemically labeled with digoxigenin were obtained commercially. The degree of labeling was different since end-labeling and the photochemical digoxigenin-labeling result in differential incorporation of label in proportion to the size of the fragment. The digoxigenin-labeled and fluorescein-labeled were bound to HRP-anti-fluorescein and AP-anti-digoxigenin and then detected with a reagent containing 2-naphthyl phosphate, peroxide, and 2,3,6-trifluorophenyl 10-methylacridan-9-carboxylate. Unlabeled DNA, dig-labeled DNA and fluorescein-labeled DNA alone were not detectable.

(a) Sample preparation

DNA digested with HindIII and labeled with either fluorescein or digoxigenin was obtained from commercial sources. Fluorescein-labeled DNA was end-labeled so that each fragment theoretically contains two labels. The digoxigenin-labeled DNA was labeled by a photochemical technique which results in the incorporation of one label for every 2–300 bases. Since the HindIII digest produces 8 fragments ranging from 125 to 23130 bp in an equimolar ratio, the digoxigenin labeling process results in differential incorporation of label in proportion to the size of the fragment.

(b) Southern Blotting Procedure

A mixture of 30 ng of digoxigenin-labeled DNA and 66 ng of fluorescein-labeled DNA restriction fragments was separated by 0.77% agarose gel electrophoresis. The electrophoresis buffer was 40 mM Tris-acetate and 2 mM EDTA (pH 8.0). MagnaGraph nylon (Micron Separations Inc., Westboro, Mass.) was soaked sequentially in water and 10× SSC for 2 and 10 min, respectively. The gel was rinsed with water, soaked in 0.25N HCl for 10 min and then treated with 0.5M NaOH/1.5M NaCl twice for 15 and 30 minutes, respectively. The gel was rinsed with water and then treated with 1M Tris-HCl (pH 7.5)/1.5M NaCl three times for 15 min each. The DNA in the gel was transferred onto the membrane by capillary blotting overnight using 10× SSC. The blots were rinsed with 5× SSC twice for 5 min each and then air-dried for 30 min followed by baking at 80° C. for 2 hours.

Figure 1:
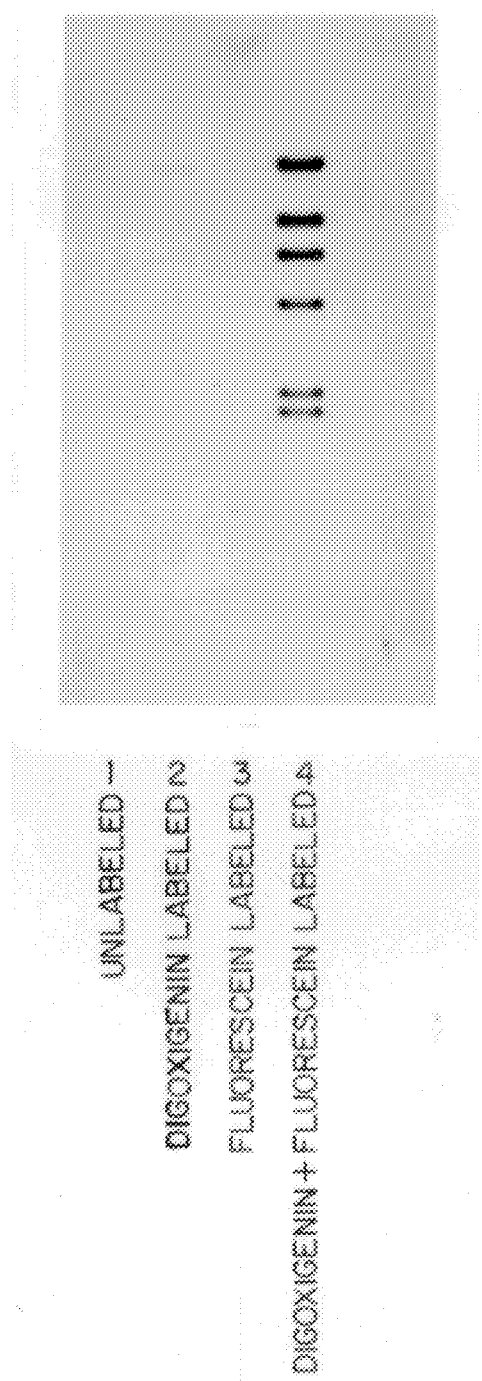
FIG. 1 is an image of an x-ray film from an experiment detecting a mixture of AP-labeled and HRP-labeled HindIII-digested DNA fragments on a nylon membrane with a chemiluminescent reagent composition. Lanes containing only one of the two sets of DNA fragments or unlabeled fragments are not detectable.

After blotting to uncharged nylon membrane and cross-linking, the blots were rinsed with TBS and then blocked with 0.5% blocking agent (Amersham) in TBS. The fragments were reacted with a mixture of HRP-anti-fluorescein antibody and AP-anti-digoxigenin antibody (Boehringer-Mannheim) in 0.5% bovine serum albumin in TBS for 40 min. The blots were washed with 0.05% Tween-TBS four times for 10 min each and then rinsed with water. The membrane was wetted with a detection reagent consisting 1 mM of the protected HRP enhancer 2-naphthyl phosphate, 0.05 mM 2,3,6-trifluorophenyl 10-methylacridan-9-carboxylate, 2.5 mM urea peroxide, 0.5% Tween 20 in 0.01M tris buffer, pH 8.8 and incubated for 25 min. Exposure of the membrane to X-ray film for 20 min produced an image of the set of bands in lane 4 of FIG. 1. As controls, lane 1 contained 94 ng of unlabeled DNA, lane 2 contained 30 ng of the digoxigenin-labeled DNA, lane 3 contained 66 ng of the fluorescein-labeled DNA.

Example 2
Specific Detection of Target DNA with Dual Probes

This example demonstrates the detection of a target ssDNA using two complementary probes. The probes were each labeled with a distinct hapten which was bound to an enzyme conjugated binding partner after the probe hybridization.
(a) Sample preparation pBR322 Plasmid DNA (United States Biochemical, Cleveland, Ohio) was linearized with EcoRI and then purified with phenol/chloroform/isoamyl alcohol (25:24:1, v/v) and then chloroform, sequentially. The DNA was then precipitated with ethanol. Two 17-mer oligonucleotides were synthesized (Genosys, The Woodlands, Texas) and purified by HPLC. The oligomers had the following sequences:

(P-2051) 5'-GAT GAG CTT TAC CGC AG-3' (SEQ ID NO:1) labeled with fluorescein at the 5'-terminus (from 2051 to 2067 on pBR322) and (P-2100)

5'-ACC TCT GAC ACA TGC AG-3' (SEQ ID NO:2) (from 2100 to 2116).

The latter 17-mer was then labeled with digoxigenin-dUTP using a DIG Oligonucleotide Tailing Kit (Boehringer-Mannheim). The yield of dig-labeled P-2100 was estimated by dot blotting with the standard dig-labeled oligonucleotide from the kit and using AP-anti-digoxigenin and NTP/X-P for colorimetry.
(b) Southern Blotting Procedure Aliquots containing 40, 20, 10 and 5 ng of linearized pBR322 plasmid DNA were electrophoresed in 0.77% agarose gel in 40 mM tris-acetate and 2 mM EDTA, pH 8.0.

MagnaGraph nylon was soaked sequentially in water and 10× SSC for 2 and 10 min, respectively. The gel was rinsed with water, soaked in 0.25N HCl for 10 min and then treated with 0.5M NaOH/1.5M NaCl twice for 15 and 30 minutes, respectively. The gel was rinsed with water and then treated with 1M Tris-HCl (pH 7.5)/1.5M NaCl three times for 15 min each. The DNA in the gel was transferred onto the membrane by capillary blotting overnight using 10× SSC. The blots were rinsed with 5× SSC twice for 5 min each and then air-dried for 30 min followed by baking at 80° C. for 2 hours.

The blots were soaked in 6× SSPE for 10 min and then prehybridized in prehybridization buffer (0.5% blocking agent, 0.1% SDS, 6× SSPE, 100 µg/mL freshly denatured herring sperm DNA) for 1 h at room temperature. The hybridization was done in the prehybridization buffer with 0.48 pmol/mL fluorescein-labeled P-2051 and 158 pmol/mL digoxigenin-labeled P-2100 for 15 h at 37° C. The blots were washed with 2.5× SSC twice for 5 min each at room temperature and then with 2.5× SSC, 0.1% SDS for 30 min at room temperature. The blots were washed with 1× SSC, 0.1% SDS twice for 15 min each at 37° C. and with 2.5× SSC for 5 min at room temperature.

Figure 2:
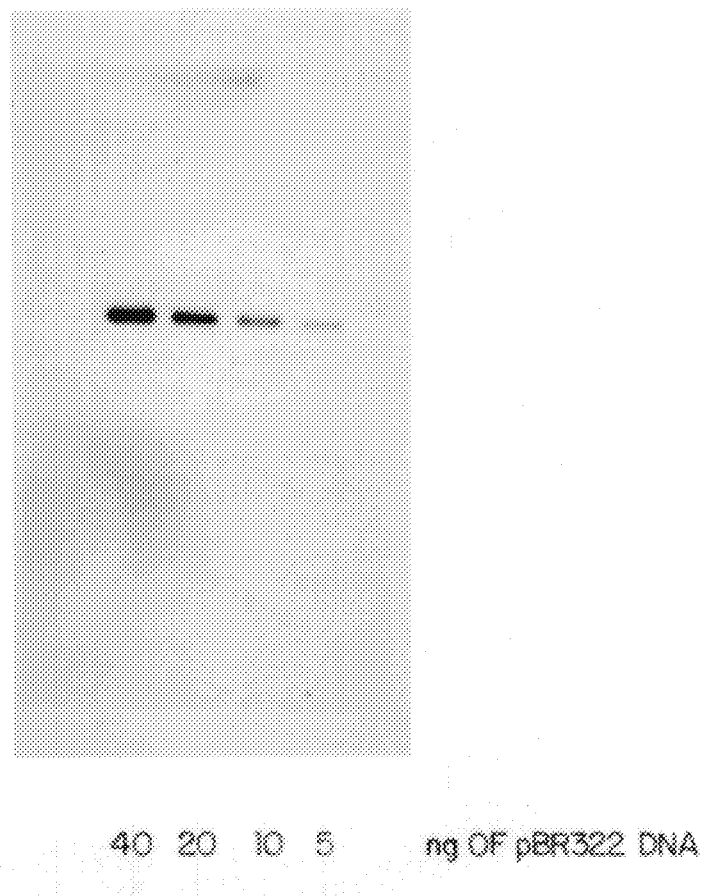
FIG. 2 is a an image of an x-ray film from an experiment detecting EcoRI-linearized pBR322 DNA hybridized to AP-labeled and HRP-labeled 17-mer probes on a nylon membrane with a chemiluminescent reagent composition containing acridan ester as the chemiluminescent peroxidase substrate.

The blots were soaked in TBS and then blocked with 0.5% blocking agent in TBS for 1 h at room temperature. The blots were rinsed with TBS and then reacted with AP-anti-digoxigenin and HRP-anti-fluorescein (Amersham) in 0.5% BSA in TBS for 45 min at room temperature. The blots were washed with 0.05% Tween-TBS four times for 10 min each and then rinsed with water. The membrane was wetted with a detection reagent consisting of 1 mM of the protected HRP enhancer 2-naphthyl phosphate, 0.05 mM 2,3,6-trifluorophenyl 10-methylacridan-9-carboxylate, 2.5 mM urea peroxide, 0.5% Tween 20 in 0.01M tris buffer, pH 8.8 and incubated for 13 min. As shown in FIG. 2, the 40, 20, 10 and 5 ng samples of linearized pBR322 DNA were clearly detected after a 13 min incubation and 10 min exposure. Controls in which one or both probes was excluded were run in parallel. Blots which lacked either the AP-labeled probe or the HRP-labeled probe produced no signal.

Figure 3:
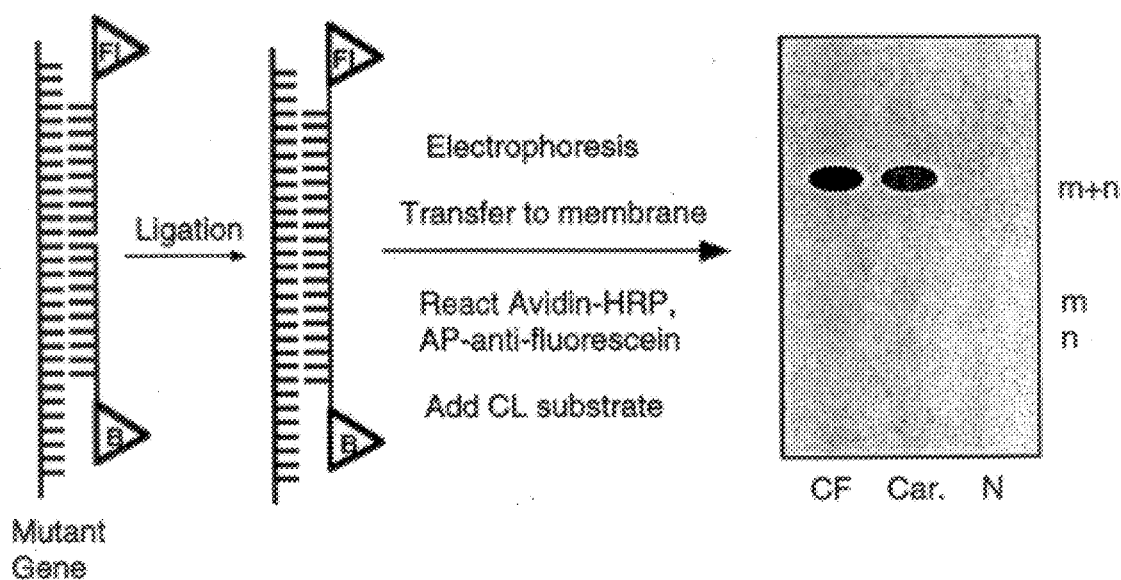
FIG. 3 is a schematic drawing of a ligation assay according to the present invention to detect the $\Delta F_{508}$ mutation in samples which are homozygous or heterozygous for the mutation and not in a sample which is homozygous normal.

Example 3
Detection of the Cystic Fibrosis ΔF508 Mutation by Ligation of Enzyme-Labeled Probes This experiment demonstrates the detection and determination of carrier status, of the CF ΔF508 mutation. The method relies on the hybridization of two differently labeled probes of n and m bases, respectively, flanking the deletion. Ligation of the adjacent bound probes in the mutant allele creates a new probe of m+n bases carrying both labels. Nonligated and ligated probes are resolved by denaturing gel electrophoresis, blotted onto a nylon membrane, reacted with enzyme-antibody conjugates and detected by the dual enzyme-catalyzed luminescence method. The method of detecting and differentiating the ΔF508 genotypes is shown schematically in FIG. 3.
(a) Chemiluminescent Substrate The chemiluminescent detection reagent comprised 0.01M tris, pH 8.8, 1 mM 2-naphthyl phosphate, 2.5 mM urea peroxide, 0.5% Tween-20, 0.3 mM 2,3,6-trifluorophenyl 10-methylacridan-9-carboxylate.
(b) DNA Samples DNA samples of the wildtype (N/N), heterozygous (N/ΔF$_{508}$) and homozygous (ΔF$_{508}$/ΔF$_{508}$) genotypes were obtained from the Coriell Cell Repositories, Camden, N.J. Samples negative for the ΔF$_{508}$ mutation were used as negative controls.
(c) Amplification of DNA by Polymerase Chain Reaction To obtain sufficient amount of DNA for the experiments, the exon 10 region (~200 bp) containing the ΔF$_{508}$ mutation was first amplified by PCR using the primers:

5' ACT TCA CTT CTA ATG ATG ATT ATG 3' (SEQ ID NO:3) and

5' CTC TTC TAG TTG GCA TGC TTT GAT 3' (SEQ ID NO:4).

The PCR was performed in 100 μl reaction consisting of 1× buffer (10 mM Tris-HCl, pH 8.3, 50 mM KCl), 200 μM of each deoxynucleotide, 1 μM of each primer, 2.5 mM MgCl$_2$, 2.5 units of Amplitaq DNA polymerase (Roche Molecular Systems, Branchburg, N.J.), and 0.5 μg of genomic DNA template. The DNA was amplified in Perkin-Elmer 480 (Norwalk, Conn.) thermal cycler for 35 cycles with an overlay of mineral oil. Each cycle consisted of 1 min each of denaturation, primer annealing, and extension at 94° C., 60° C. and 72° C., respectively, with a 10 min extension at the end of cycling. Prior to the cycling, the template DNA was denatured at 95° C. for 3 min, quickly cooled on ice and added to the PCR reaction tube. Specific amplification of the correct size product was confirmed on an 1% agarose gel containing ethidium bromide.

The amplified DNA was purified using QIAquick purification kit (QIAGEN, Chatsworth, Calif.) to remove unincorporated deoxyribonucleotides and oligonucleotide primers. Purified DNA was quantitated spectrophoto-metrically before use in the ligation and hybridization experiments described below.

(d) Ligation Reaction, Electrophoresis and Transfer

The detection of $\Delta F_{508}$ mutation and differentiation of genotypes is based on the ability to ligate a pair of oligonucleotides that anneal to the template next to each other on either side of the mutation in N/$\Delta F_{508}$ and $\Delta F_{508}/\Delta F_{508}$ genotypes. In the N/N (wildtype) genotype, on the other hand, the annealed oligonucleotides do not ligate to each other because they are separated by a gap resulting from the presence of three intervening nucleotides.

Two oligonucleotides, one labeled with biotin and the other with fluorescein, and differing in length by three nucleotides (21 and 24mers) were designed to anneal to the sense strand of the DNA template and are designated antisense upstream:

(5' biotin-TAT TCA TCA TAG GAA ACA CCA 3' (SEQ ID NO:5)) and antisense downstream:

(5' phosphate-ATG ATA TTT TCT TTA ATG GTG CCA- (SEQ ID NO:6) Fluorescein-3').

The antisense downstream oligonucleotide was synthesized with 5'-phosphate to facilitate its enzymatic ligation to the antisense upstream oligonucleotide. The ligation reaction consisted of 200 ng of purified PCR amplified template of each genotype, 10 ng each of the oligonucleotides, 1× ligation buffer (30 mM Tris-HCl, pH 7.8, 10 mM MgCl$_2$, 10 mM DTT and 0.5 mM ATP) and 5 units of T4 DNA ligase. These concentrations of the template and the oligonucleotides provided for optimum discrimination of genotypes. The template-oligonucleotide mix was first heated at 95° C. for 3 min and quickly cooled on ice before adding to it the ligation buffer and ligase. The ligations were performed in 20 μl reaction at 15° C. overnight. A negative control ligation reaction of the labeled oligonucleotides in the absence of template was also performed. The ligation reactions were fractionated on 16% or 20% denaturing polyacrylamide gels (7M Urea) along with a dual labeled (biotin and fluorescein) oligo-nucleotide as size marker (45mer). The electrophoresed ligation reactions were capillary transferred onto a 0.2 μM MagnaGraph nylon membrane in 10× SSC (1.5M NaCl, 0.15M sodium citrate, pH 7.2). The blotted membrane was baked at 80° C. for 2 h.

(e) Enzyme Conjugate and Chemiluminescent Substrate Treatments

The membranes were first washed for 15 min in 1× wash buffer (0.1M maleic acid, 0.15M NaCl, pH 7.5, 0.3% Tween 20) and blocked for 1 h in 2% blocking buffer (Blocking Reagent—Boehringer Mannheim, Indianapolis, Ind., dissolved in 0.1M maleic acid, 0.15M NaCl, pH 7.5). The membrane with the ligation products was incubated for 30 min in anti-fluorescein-AP (Boehringer Mannheim) and Avidin-HRP (Pierce, Rockford, Ill). The working concentrations of all the enzyme conjugates were 1:5000 dilutions in 2% blocking buffer. Following treatment with the enzyme conjugate, the membranes were washed twice for 20 min each in 1× wash buffer and then reacted with the chemiluminescent substrate for 5 min in the dark.

Excess substrate from the membrane was removed by placing and gently pressing the membrane between transparency films. The membrane was then exposed to X-ray film for a time period, generally ranging from a few seconds to minutes, to obtain optimal signal and background.

(f) Chemiluminescent Detection

As shown in FIG. 4, the ligated oligonucleotide products containing both labels are present only in the N/$\Delta F_{508}$ (lane 5) and $\Delta F_{508}/\Delta F_{508}$ (lane 6) genotypes but not in the wildtype (lane 4). Further, the ligated product in the N/$\Delta F_{508}$ genotype is less intense than in the $\Delta F_{508}/\Delta F_{508}$. This is expected because the heterozygote contains only one copy of the allele with $\Delta F_{508}$ as compared to two alleles in the homozygote.

When the ligation reactions were electrophoresed for a short distance on a 16% gel (until the bromophenol blue was half way into the gel), the unligated oligonucleotides bearing different labels stayed together yielding the chemiluminescent signal (FIG. 4A) in lanes 4 and 5. In another experiment, a 20% gel was electrophoresed distance sufficient to separate the 21mer and 24mer. In this case, bands corresponding to the unligated probes were not detected in lanes 4 and 5 (FIG. 4B).

As shown here, the ligation method of detection is template dependent and mutation specific. The simple procedure of denaturation of template, annealing of the oligonucleotides to the template by cooling on ice, and ligation at 15° C. resulted in specific ligation of oligonucleotides in the genotypes carrying the mutation; and no non-specific ligation products were seen with the wildtype template and in the absence of template (negative control). Modification of the procedures described below such as ligation at higher temperatures and/or for shorter periods, crosslinking of blotted DNA by ultraviolet irradiation rather than baking may be employed. In addition, we have found that nylon membrane of 0.2 μM pore size retains oligonucleotides better than the more commonly used 0.45 μM membrane.

Example 4

Detection of the Cystic Fibrosis $\Delta F508$ Mutation by Hybridization of Enzyme-Labeled Probes The hybridization method of detecting and differentiating the $\Delta F508$ genotypes is shown schematically in FIG. 5.

(a) Southern Transfer and Hybridization

In the hybridization method of detection and differentiation of $\Delta F508$ genotypes, a pair of differentially labeled (biotin and digoxigenin) oligonucleotide probes, one complementary to the normal and the other to the mutant allele, were hybridized simultaneously to the membrane bound DNA templates and reacted sequentially with the antibody-enzyme conjugates followed by the chemiluminescent substrate. The labeled oligonucleotides are 5' biotin—ATA TCA TCT TTG GTG TTT CCT 3' (SEQ ID NO:7) (normal) and 5' digoxigenin—GAA AAT ATC ATT GGT GTT TCC 3' (SEQ ID NO:8) (mutant). The oligonucleotides were custom synthesized by Oligos etc., (Wilsonville, Oreg.).

The amplified PCR products of each genotype (100 ng) were electrophoresed on a 1% agarose gel for a short distance (1 cm) so that the PCR products of normal and ΔF508 alleles differing by three nucleotides migrate as a single band. The gel was depurinated (0.25M HCl), denatured (0.5N NaOH, 1.5M NaCl), neutralized (0.5M Tris-HCl, pH 7.5, 3M NaCl), and vacuum blotted onto a neutral nylon membrane (Hybond N, Amersham, Arlington Heights, Ill.). The blotted membrane was baked at 80° C. for 2 hours and hybridized with the biotin and digoxigenin labeled oligonucleotide probes as described below.

The blot was prehybridized and hybridized at 52° C. for 1 h and overnight, respectively, using a buffer containing 6× SSC (0.9M sodium chloride, 0.09M sodium citrate, pH 7.0), 0.01M EDTA, pH 8.0, 5× Denhardt's solution (0.1% Ficoll Type 400, 0.1% polyvinylpyrrolidone, 0.1% bovine serum albumin), 0.5% SDS and 100 ug/ml denatured salmon sperm DNA (GIBCO BRL, Life Technologies, Gaithersburg, Md.). The post-hybridization washes were done at 52° C. for 20 minutes each in 2× SSC, 0.1% SDS and 0.5× SSC, 0.1% SDS.

(b) Enzyme Conjugate and Chemiluminescent Substrate Treatments

The membranes of the hybridization experiments were first washed for 15 min in 1× wash buffer (0.1M maleic acid, 0.15M NaCl, pH 7.5, 0.3% Tween 20) and blocked for 1 h in 2% blocking buffer (Boehringer Mannheim). The hybridized membrane was treated for 30 min with anti-digoxigenin-AP (Boehringer Mannheim) and Avidin-HRP. The working concentrations of all the antibody-enzyme conjugates were 1:5000 dilutions in 2% blocking buffer. Following the antibody-enzyme treatment, the membranes were washed twice for 20 min each in 1× wash buffer and then reacted with the chemiluminescent substrate for 5 min in the dark. Excess substrate from the membrane was removed by placing and gently pressing the membrane between transparency films. The membrane was then exposed to an X-ray film for a time period, generally ranging from a few seconds to minutes, to obtain optimal signal and background.

(c) Chemiluminescent Detection

As shown in FIG. 6, a strong chemiluminescent signal is emitted in the heterozygous (N/ΔF508) genotype (lane 2) when hybridized with a pair of differentially labeled oligonucleotide probes, one complementary to the normal allele and the other to the ΔF508 mutant allele. The wildtype and ΔF508/ΔF508 genotypes (lanes 1 and 3), on the other hand, are negative as expected indicating that only one of the oligonucleotide probes, complementary to either the normal or mutant allele hybridized to the genotypes.

Example 5
Random testing of specimens of non-cystic fibrosis individuals

Both the ligation and hybridization methods were used to test DNA specimens of unknown CF genotype for $\Delta F_{508}$ mutation using the method of Example 3 and 4. None of the four specimens tested produced positive signals by either the ligation and hybridization methods indicating lack of the $\Delta F_{508}$ mutation. Conversely, known heterozygotes yielded a strong positive signal by both methods.

Example 6
Simultaneous Detection of Two Infectious Agents

The dual substrate and probe systems presented here can also be utilized for the detection of more than one nucleic acid entity such as the presence of two different infectious agents in a clinical specimen. Sequence specific oligonucleotide probes are designed to a gene sequence that is unique to each of the infectious agent. One probe is labeled with digoxigenin and the other with fluorescein. For increased sensitivity, the target DNA of the specimen can be amplified by PCR. The probes are hybridized to their respective target DNA, extracted from a clinical specimen, which is either bound to a nylon membrane or is in solution. In the solution hybridization format, it is imperative that the amplified DNA target is biotinylated (by using the biotinylated primers for the amplification) so that the hybridized probe-target DNA complexes are captured onto streptavidin coated microtiter wells. Following post-hybridization washes to remove non-specifically bound probes, the hybridized DNA is treated with anti-hapten AP and HRP antibodies followed by reacting with the dual substrate for chemiluminescent detection.

Example 7
Detection of Gene Rearrangements

The dual substrate and probe methods of the present invention are utilized for the detection of gene rearrangements where two DNA segments are fused as a consequence of a chromosomal translocation. In the normal human cell, the genes are on separate chromosomes. Following the chromosomal translocation the genes are fused to form a contiguous piece of DNA.

The target gene regions involved in the gene rearrangement are amplified by PCR using a forward sense primer of gene 1 and a reverse antisense primer of gene 2. This primer pair amplifies only the contiguous DNA resulting from the gene rearrangement and no amplification results from the untranslocated DNA. The size of this amplified DNA will depend on the site of interchange between the two genes involved in the translocation.

The detection of the amplified target can be acheived in two ways. In one format, the target is immobilized in wells of a streptavidin coated microtiter well in which case the primers used for the amplification are labeled with biotin. In an alternate format, the amplified product is immobilized on a nylon membrane without the need to use biotinylated primers for amplification. Next the target is hybridized to a digoxigenin-labeled probe to gene 1 and a fluorescein-labeled probe to gene 2. The membrane or well is blocked to prevent non-specific binding of antibodies and then anti-digoxigenin-AP and anti-fluorescein-HRP antibodies are bound to the immobilized probes as described above. After washing, the reagent of Example 3 is added and chemiluminescence detected with x-ray film or a CCD camera when the method is performed on a blotting membrane or with a microtiter plate luminometer when the method is performed in a microtiter plate. The specimen with gene rearrangement is positively identified with the chemiluminescent signal.

The hybridization and ligation formats used can be adapted for automation to reduce turnaround time which is desirable for clinical laboratory setting.

Example 8
Western Blot Assay Using Dual Enzyme Labels

The dual substrate and probe systems presented here was utilized in a Western blot assay of the HIV γ-gp120protein. The assay format is shown in FIG. 7.

Materials and Methods

Affinity purified rabbit IgG anti-mouse IgG2a-AP conjugate and sheep IgG anti-rabbit IgG-peroxidase conjugate were obtained from Cappel Products (Durham, N.C.). HIV-1-γgp120 (50 μg/500 μL) and mouse IgG2a anti-human HIV-1-γgp120 (MAb1CL) (100 μg/100 μL) were from Repligen (Cambridge, Mass.). The HIV-1-γgp120 and IgG samples were centrifuged at 10,000 g for 2 min and the supernatant was used in the immunological reaction.

IMMOBILON-P PVDF membrane was from Millipore (Bedford, Mass.)

SDS-PAGE was performed utilizing the buffer system described by Laemmli (U. K. Laemmli, Nature (London), 227, 680–5 (1970)). The stacking gel was 4.38% acrylamide 0.12% bisacrylamide. The separating gel was 6.81% acrylamide: 0.19% bisacrylamide. Following electro-phoresis, the gel was equilibrated for 7–8 min with the transfer buffer which contained 20 mmol/L Tris, 153 mmol/L glycine and 20% (v/v) methanol. The gel, sandwiched between a sheet of membrane and a sheet of Whatman 3 MM chromatography paper, was placed in the transfer unit (Bio-Rad Laboratories, Richmond, Calif.). The proteins in the gel were electroeluted for 25 min at 40° C. at 100 V constant voltage. The membrane was then placed in 50 mmol/L Tris-HCl buffered saline at pH 7.4 (TBS) at 4° C. overnight. After this period the membrane was washed twice with TBS for 10 min each.

Blocking was performed with 0.05% Tween-20 in TBS, pH 7.4 (T-TBS) containing 1% non-fat powdered milk (NFM) for 1 h at room temperature. The blocked membrane was incubated for 90 min at room temperature with 1° antibody (1:250 dilution of mouse IgG2a anti-human HIV-1-γgp120) using T-TBS containing 1% NFM. The membrane was then rinsed and washed three times for 5 min each with T-TBS at room temperature. The washed membrane was incubated for 75 min at room temperature with 2° antibody (1:250 dilution of rabbit IgG anti-mouse IgG2a-AP) using T-TBS containing 1% NFM. The membrane was rinsed and washed four times for 5 min each with T-TBS. The washed membrane was next incubated for 60 min at room temperature with 3° antibody (1:20,000 dilution of sheep IgG anti-rabbit IgG-peroxidase) using T-TBS containing 1% NFM. The membrane was rinsed and washed four times for 5 min each with T-TBS followed by a 5 min wash with TBS. The washed membrane was incubated in the detection reagent of Example 1 for 10 min, drained and placed between sheets of transparency film.

The amount of antigen loaded in the five lanes of the gel was 1) 8 ng, 2) 4 ng, 3) 2 ng, 4) 1 ng, 5) 0.5 ng. As can be seen from FIG. 8, all five bands were clearly detectable over the background in a 3 min exposure less than one hour after the membrane was contacted with detection reagent. Images could be easily obtained over the course of a day. Additional experiments under identical conditions have demonstrated detection of 30 pg in under 3 hours.

The specificity of the assay was evaluated by performing it without the HRP-antibody conjugate in one experiment and without the AP-antibody conjugate in another experiment. No signal was detected for any of the five bands in each experiment. In addition, an experiment using both enzyme-labeled antibodies but omitting the 2-naphthyl phosphate from the detection reagent also produced no signal.

Example 9

Immunoassay Using Dual Enzyme Labels

A procedure for a sandwich immunoassay for the detection of hCG according to the methods of the present invention is as follows. Mouse anti-hCG antibody (Sigma) is labeled with HRP by the glutaraldehyde method. Another portion of mouse anti-hCG antibody is conjugated to AP by the periodate method or using a bifunctional coupling agent containing succinimide and maleimide moieties. The wells of a white microplate are coated with mouse anti-hCG antibody-HRP conjugate, washed and aspirated. Aliquots of hCG standards and samples are added and incubated for 1 h. The wells are washed 3× and aspirated. The wells are incubated a solution containing mouse anti-hCG antibody-AP conjugate and 0.1% blocking agent for 1 h, washed 3× and aspirated. The detection reagent of Example 1 is added and chemiluminescence intensity measured at 10 min.

What is claimed is:

1. A method for simultaneously detecting a first and second target species in a sample suspected of containing both the first and second target species by a single chemiluminescent reaction comprising:
   (a) contacting the sample with a first specific binding partner which binds to the first target species and a second specific binding partner which binds to the second target species to thereby form a first binding pair and a second binding pair;
   (b) providing a hydrolytic enzyme as a label for the first binding partner and providing a peroxidase enzyme as a label for the second binding partner;
   (c) providing for reaction with the first and second binding pair a chemiluminescent peroxidase substrate, a peroxide compound and a protected enhancer compound of the formula ArOX wherein X is a group which is removable by the hydrolytic enzyme to produce a phenolic enhancer compound ArOH which enhances the activity of the peroxidase enzyme;
   (d) allowing the hydrolytic enzyme to react with the protected enhancer compound to produce the enhancer compound which enhances the activity of the reaction of the peroxidase with the peroxide and the peroxidase substrate and thereby producing chemiluminescence; and
   (e) measuring the chemiluminescence produced, wherein the presence of chemiluminescence indicated the presence of both target species in the sample.

2. The method of claim 1 wherein the first specific binding partner is labeled with a first hapten, wherein the second specific binding partner is labeled with a second hapten which is different from the first hapten and wherein the hydrolytic enzyme is provided as a conjugate with an antibody which binds to the first hapten and wherein the peroxidase enzyme is provided as a conjugate with an antibody to the second hapten.

3. The method of claim 2 wherein the first and second haptens are selected from the group consisting of biotin, fluorescein and digoxigenin and wherein the first hapten is different from the second hapten.

4. The method of claim 1 wherein the first specific binding partner is labeled with biotin and one of the hydrolytic enzyme or the peroxidase enzyme is provided as a conjugate with avidin or streptavidin.

5. The method of claim 1 wherein the first specific binding partner is directly labeled with the hydrolytic enzyme and the second specific binding partner is directly labeled with the peroxidase enzyme.

6. The method of claim 1 wherein the first and second target species comprise a first region of a nucleic acid and a second region of a nucleic acid and wherein the first specific binding partner is a first oligonucleotide probe complementary to the first region of the nucleic acid and the second specific binding partner is a second oligonucleotide probe complementary to the second region of the nucleic acid.

7. The method of claim 6 used to detect a chromosomal translocation.

8. The method of claim 1 wherein the first and second target species comprise a first nucleotide sequence of a normal gene and a second nucleotide sequence containing a mutation of the gene, wherein the first specific binding partner is an oligonucleotide probe complementary to the nucleotide sequence of the normal gene and the second specific binding partner is an oligonucleotide probe complementary to the nucleotide sequence of the mutation-containing gene.

9. The method of claim 8 used for determining whether the sample contains the genes from a carrier of a recessive genetic disease.

10. The method of claim 9 wherein the recessive disease is cystic fibrosis.

11. The method of claim 1 wherein the first and second target species are first and second epitopes of an antigen and wherein the first specific binding partner is an antibody which binds the first epitope and the second specific binding partner is a different antibody which binds the second epitope.

12. The method of claim 11 used in a sandwich immunoassay.

13. The method of claim 11 used in a Western blot assay.

14. The method of claim 1 wherein the peroxidase enzyme is horseradish peroxidase.

15. The method of claim 1 wherein the hydrolytic enzyme is selected from the group consisting of alkaline phosphatase, β-galactosidase, β-glucosidase, β-glucuronidase and carboxyl esterase.

16. The method of claim 15 wherein the hydrolytic enzyme is alkaline phosphatase.

17. The method of claim 1 conducted on the surface of a solid support.

18. The method of claim 12 wherein the solid support is selected from the group consisting of test strips, blotting membranes, filters, microwells, test tubes and beads.

19. The method of claim 1 wherein the enhancer compound ArOH formed by reaction of ArOX with the hydrolytic enzyme is selected from the group consisting of p-phenylphenol, p-iodophenol, p-bromophenol, p-chlorophenol, 2,4-dichloro-phenol, p-imidazolylphenol, p-thiazolylphenol, p-hydroxy-acetanilide, p-hydroxycinnamic acid, (p-cyanomethyl-thio)-phenol, ring halogenated derivatives of (p-cyanomethyl-thio)-phenol, phenolindophenol, 2-naphthol, 6-bromo-2-naphthol, 6-hydroxybenzothiazole, 2-cyano-6-hydroxy-benzothiazole, firefly luciferin and dehydroluciferin.

20. The method of claim 1 wherein X of the compound of the formula ArOX is selected from the group consisting of a residue of a phosphate group, a β-galactoside group, a β-glucoside group, a β-glucuronide group and a carboxyl ester group.

21. The method of claim 20 wherein X is a $PO_3^{2-}$ salt group.

22. The method of claim 1 wherein the protected enhancer is selected from the group consisting Of $PO_3^{2-}$ salts of p-phenylphenol, p-iodophenol, p-bromophenol p-chloro-phenol, 2,4-dichloro-phenol, p-imidazolylphenol, p-thiazolylphenol, p-hydroxy-acetanilide, p-hydroxycinnamic acid, (p-cyanomethylthio)-phenol, ring halogenated derivatives of (p-cyanomethylthio) -phenol, phenolindo-phenol, 2-naphthol, 6-bromo-2-naphthol, 6-hydroxy-benzothiazole, 2-cyano-6-hydroxy-benzothiazole, firefly luciferin and dehydroluciferin.

23. The method of claim 1 wherein the chemiluminescent peroxidase substrate is selected from the group consisting of hydroxy-substitute d dihydrophthalazinediones, amino-substituted dihydrophthalazinediones and alkylacridan-9-carboxylate derivatives having the general formula:

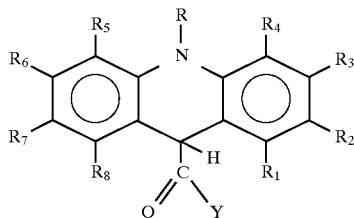

wherein R is selected from alkyl, heteroalkyl and aralkyl groups, wherein $R_1$ to $R_8$ are selected independently from groups which allow the production of light and wherein adjacent pairs of groups $R_1$ to $R_8$ can constitute the group CH=CH—CH=CH thereby forming a benzo-fused ring and wherein Y is an ester, thioester or sulfonimide leaving group.

24. The method of claim 23 wherein the chemiluminescent peroxidase substrate is selected from the group consisting of luminol, 5-hydroxyphthalazinedione and an acridancarboxylate derivative having the formula:

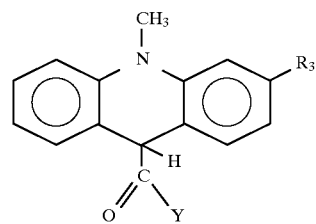

wherein and wherein $R_3$ is H or a methoxy group.

25. The method of claim 24 wherein Y is a 2,3,6-trifluorophenoxy group.

26. The method of claim 1 wherein the peroxide is selected from the group consisting of hydrogen peroxide, urea peroxide and perborate salts.

27. The method of claim 1 wherein the chemiluminescent peroxidase substrate, the peroxide and the protected enhancer are provided in an aqueous reagent composition.

28. The method of claim 27 wherein the composition further comprises a suppressing agent which reduces background chemiluminescence from the reagent composition.

29. The method of claim 28 wherein the background suppressing agent is selected from the group consisting of nonionic surfactants, nonionic water-soluble polymers, polyether polyols, proteins, serum albumin and non-fat milk.

* * * * *